US011525995B2

(12) United States Patent
Kumagai et al.

(10) Patent No.: US 11,525,995 B2
(45) Date of Patent: Dec. 13, 2022

(54) IMAGING SYSTEM

(71) Applicant: YAMAHA HATSUDOKI KABUSHIKI KAISHA, Iwata (JP)

(72) Inventors: Takahiko Kumagai, Shizuoka (JP); Yohei Izume, Shizuoka (JP)

(73) Assignee: YAMAHA HATSUDOKI KABUSHIKI KAISHA, Iwata (JP)

( * ) Notice: Subject to any disclaimer, the term of this patent is extended or adjusted under 35 U.S.C. 154(b) by 698 days.

(21) Appl. No.: 16/492,111

(22) PCT Filed: Feb. 2, 2018

(86) PCT No.: PCT/JP2018/003705
§ 371 (c)(1),
(2) Date: Sep. 7, 2019

(87) PCT Pub. No.: WO2018/163683
PCT Pub. Date: Sep. 13, 2018

(65) Prior Publication Data
US 2020/0326525 A1      Oct. 15, 2020

(30) Foreign Application Priority Data

Mar. 10, 2017    (JP) .............................. JP2017-046409

(51) Int. Cl.
*G02B 21/36*     (2006.01)
*H04N 5/232*     (2006.01)
(Continued)

(52) U.S. Cl.
CPC ....... *G02B 21/365* (2013.01); *H04N 5/23212* (2013.01); *G01N 21/17* (2013.01);
(Continued)

(58) Field of Classification Search
CPC .... G02B 21/06; G02B 21/241; G02B 21/365; G02B 21/367; G02B 6/12028; G02B 7/38; H04N 5/23212
See application file for complete search history.

(56) References Cited

U.S. PATENT DOCUMENTS

| 5,959,724 A | 9/1999 | Izumi et al. |
| 6,067,147 A | 5/2000 | Hirabayashi et al. |
| (Continued) | | |

FOREIGN PATENT DOCUMENTS

| CN | 101048492 A | 10/2007 |
| CN | 102713713 A | 10/2012 |
| (Continued) | | |

OTHER PUBLICATIONS

"Automated Selection and Placement of Single Cells Using Vision-Based Feedback Control"—Yasser H. Anis, Mark R. Holl, and Deirdre R. Meldrum; IEEE Transactions on Automation Science and Engineering, vol. 7, No. 3, Jul. 2010 (Year: 2010).*
(Continued)

*Primary Examiner* — Mainul Hasan
(74) *Attorney, Agent, or Firm* — Studebaker & Brackett PC

(57) ABSTRACT

An imaging system includes an imaging device configured to image an imaging subject on an imaging optical axis, and a calculation unit configured to acquire data relating to a position and/or a size of the imaging subject based on image information acquired by the imaging device through the imaging. The calculation unit acquires change information relating to condition change in the imaging and/or change in the imaging subject on the image. The change is caused by interposition of a light transmitting member when the light transmitting member is interposed on the imaging optical
(Continued)

axis during the imaging, and the calculation unit corrects the data based on the change information.

8 Claims, 12 Drawing Sheets

(51) Int. Cl.
*G01N 21/17* (2006.01)
*G02B 21/06* (2006.01)
*G02B 6/12* (2006.01)
*G02B 7/38* (2021.01)

(52) U.S. Cl.
CPC ............ *G02B 6/12028* (2013.01); *G02B 7/38* (2013.01); *G02B 21/06* (2013.01)

(56) References Cited

U.S. PATENT DOCUMENTS

| | | |
|---|---|---|
| 7,423,673 B1 | 9/2008 | Efrat et al. |
| 2008/0273786 A1 | 11/2008 | Komori et al. |
| 2009/0086314 A1* | 4/2009 | Namba ................ G02B 21/34 359/383 |
| 2011/0085786 A1 | 4/2011 | Tamaki |
| 2012/0140055 A1 | 6/2012 | Narusawa et al. |
| 2013/0329034 A1 | 12/2013 | Eguchi et al. |
| 2014/0168503 A1 | 6/2014 | Maruyama |
| 2015/0278625 A1* | 10/2015 | Finkbeiner ........... G06V 20/693 348/79 |
| 2015/0362716 A1* | 12/2015 | Kei ....................... G06V 20/693 435/288.7 |
| 2016/0304821 A1 | 10/2016 | Ito |
| 2016/0357002 A1* | 12/2016 | Suzuki ................. G02B 21/244 |
| 2017/0070725 A1 | 3/2017 | Kishiwada et al. |
| 2017/0128932 A1 | 5/2017 | Ito et al. |
| 2017/0131308 A1 | 5/2017 | Ito et al. |
| 2017/0131315 A1 | 5/2017 | Ito et al. |
| 2017/0159002 A1 | 6/2017 | Ito |
| 2017/0167955 A1 | 6/2017 | Ito et al. |
| 2019/0141313 A1 | 5/2019 | Kishiwada et al. |
| 2019/0187450 A1* | 6/2019 | Hirata .................... G02B 21/26 |
| 2020/0013146 A1 | 1/2020 | Yasuda |
| 2020/0025677 A1* | 1/2020 | Prater ...................... G01J 3/44 |

FOREIGN PATENT DOCUMENTS

| | | |
|---|---|---|
| CN | 103687468 A | 3/2014 |
| CN | 106459864 A | 2/2017 |
| CN | 106459865 A | 2/2017 |
| CN | 106459866 A | 2/2017 |
| JP | H07-333668 A | 12/1995 |
| JP | H11083475 A | 3/1999 |
| JP | 2005-024599 A | 1/2005 |
| JP | 2005-207986 A | 8/2005 |
| JP | 2009-162974 A | 7/2009 |
| JP | 4578814 B2 | 11/2010 |
| JP | 2012123039 A | 6/2012 |
| JP | 2013148441 A | 8/2013 |
| JP | 2013170861 A | 9/2013 |
| JP | 2013254108 A | 12/2013 |
| JP | 2015169583 A | 9/2015 |
| JP | 2016-014974 A | 1/2016 |
| WO | 2010/126903 A1 | 11/2010 |
| WO | 2015087371 A1 | 6/2015 |
| WO | 2018/012130 A1 | 1/2018 |

OTHER PUBLICATIONS

"Automated Selection and Placement of Single Cells Using Vision-Based Feedback Control"—Anis et al., IEEE Transactions on Automation Science and Engineering, vol. 7, No. 3, Jul. 2010. (Year: 2010).*

"Automated Vision-based Selection and Placement of Single Cells in Microwell Array Formats"—Anis et al., 4th IEEE Conference on Automation Science and Engineering; Key Bridge Marriott, Washington DC, USA; Aug. 23-26, 2008 (Year: 2008).*

International Search Report issued in PCT/JP2018/003705; dated May 1, 2018.

The extended European search report issued by the European Patent Office dated Feb. 4, 2020, which corresponds to European Application No. 18764384.6-1020 and is related to U.S. Appl. No. 16/492,111.

Daniel Iwaniuk et al. "Correcting spherical aberrations induced by an unknown medium through determination of its refractive index and thickness", Sep. 26, 2011, vol. 19, No. 20, Optics Express, XP055659252.

* cited by examiner

CHANGE RATE IN X DIRECTION = rx / Rx
CHANGE RATE IN Y DIRECTION = ry / Ry

IMAGING SYSTEM

CROSS-REFERENCE TO RELATED APPLICATIONS

This application is a National Stage of International Patent Application No. PCT/JP2018/003705, filed Feb. 2, 2018, which claims benefit from JP 2017-046409, filed Mar. 10, 2017, the entire content of each are incorporated herein by reference.

BACKGROUND

Technical Field

The present disclosure relates to an imaging system that images an imaging subject with a light transmitting member interposed on an imaging optical axis.

Background Art

Occasionally, imaging of a cell (or a cell aggregate) is required for, for example, medical and biological research use. An operation is carried out in which, for example, cells are scattered on a dish having a lot of accommodation recesses and desired cells are selected and transferred to a microplate. For the selection, the dish carrying the cells are imaged by an imaging device and the cell are classified into usable cells and unusable cells and foreign matters using, for example, an imaging processing technique.

A tip having a tip end opening that suctions and discharges a cell is used to transfer the cell to the microplate. The tip is attached to a tip end of a head that is able to move in the vertical and horizontal directions and that is connected to a negative pressure mechanism. An accurate determination of the position of the tip end opening is required to carry out appropriate suction and discharge. Japanese Patent No. 4578814 discloses a technique of imaging a nozzle (corresponding to the tip) by an imaging device and determining a position of the tip end of the nozzle using an autofocus mechanism.

In the imaging of the cells and the tip described above, a light transmitting member is required to be interposed on an imaging optical axis of the imaging device, in some cases. For example, when cells carried in a transparent dish are imaged from a bottom surface side of a transparent container retaining the dish, an image of the cells is acquired through the transparent container and the dish. When the transparent container is placed on a transparent base, the image of the cells is acquired through the base additionally. The imaging through the base is also required for the imaging of the tip end opening of the tip, sometimes. In these cases, the position and size of the cells and the position of the tip end opening of the tip are not accurately determined because of the interposed light transmitting member such as the container and the base that causes refraction of optical path.

SUMMARY

Accordingly, the present disclosure provides an imaging system that can accurately determine a position and/or a size of an imaging subject even when the imaging subject is imaged with a light transmitting member interposed on an imaging optical axis.

One aspect of the present disclosure provides an imaging system including an imaging device configured to image an imaging subject on an imaging optical axis; and a calculation unit configured to acquire data relating to a position and/or a size of the imaging subject based on image information acquired by the imaging device through the imaging, in which the calculation unit acquires change information relating to condition change in the imaging and/or change in the imaging subject on the image. The change is caused by interposition of a light transmitting member when the light transmitting member is interposed on the imaging optical axis during the imaging, and the calculation unit corrects the data based on the change information.

DETAILED DESCRIPTION

An embodiment of the present disclosure will be described in detail below with reference to the drawings. Although not restricted thereto, as particularly favorable, an exemplified imaging subject for an imaging system according to the present disclosure is cells or cell aggregates (spheroid) derived from the living body. Each cell aggregate derived from the living body is formed by several to hundreds of thousands of aggregated cells. Thus, the cell aggregates each have a different size. Each cell aggregate formed by living cells has a substantially spherical shape; however, the cell aggregate sometimes has a distorted shape or has an uneven density when part of the cells forming the cell aggregate are denatured or become dead cells. In some tests in the field of biotechnology and medicine, a cell transfer device is used that picks with a tip thereof a usable cell aggregate among a plurality of cell aggregates that have different shapes and are carried in a dish on a selecting stage and transfers the selected cells to a microplate. A variety of processing is applied to the cell aggregate on the microplate, including observation, drug efficacy check, inspection, culturing etc. In the following description, the cell aggregates are included in and expressed as cells C, in general.

An imaging system is applied to the cell transfer device described above to determine height positions of the tip, dish and cell C or to determine the shape of the cell C based on image information. Exemplified application of an imaging system according to the present disclosure at each location/section in the cell transfer device will be described below.

[Entire Structure of Cell Transfer Device]

Figure 1:
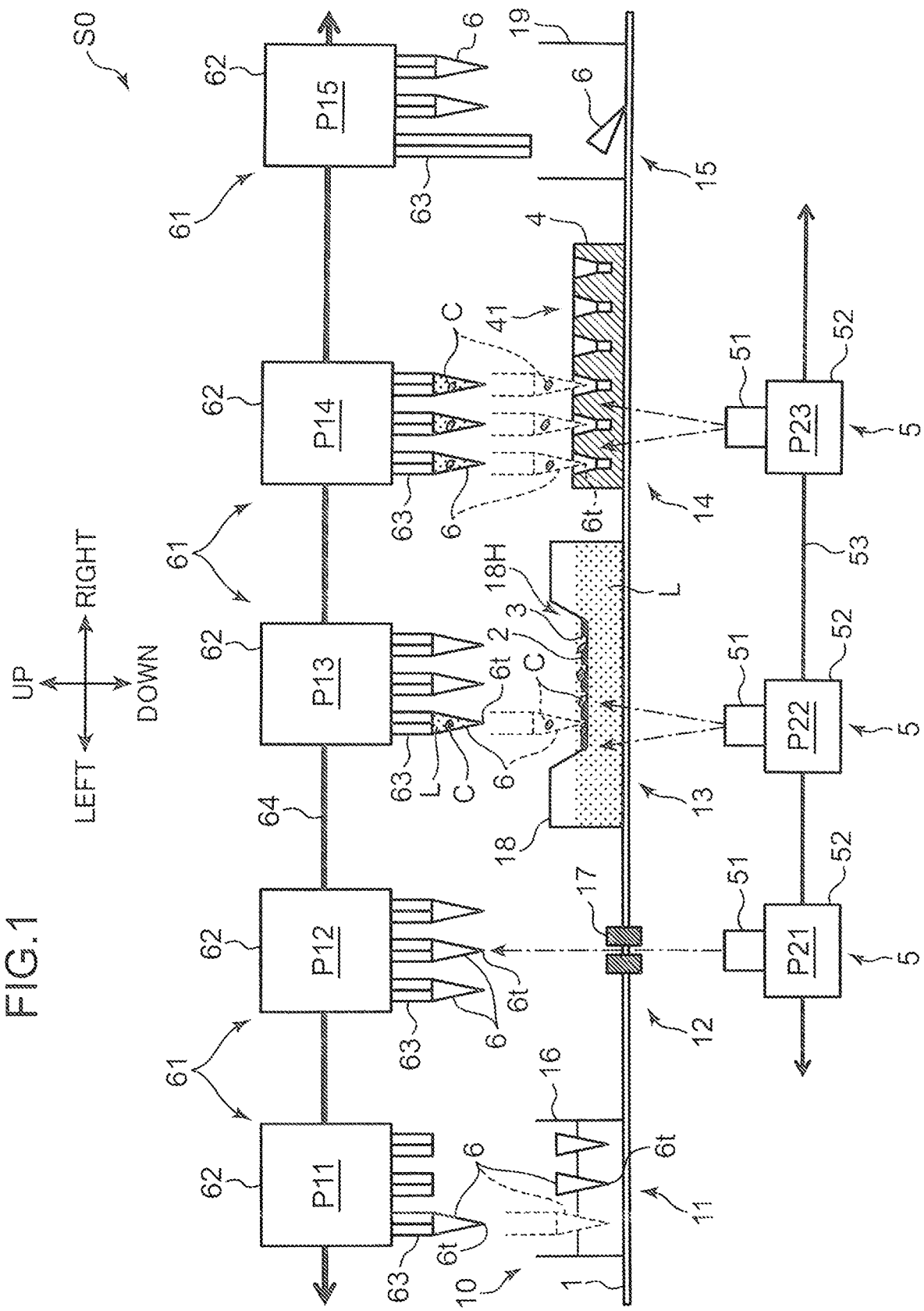
FIG. 1 is a schematic view showing an exemplified configuration of a cell transfer device.

First, the entire structure of a cell transfer device S0 will be described schematically with reference to FIG. 1. The cell transfer device S0 includes a base 1 (light transmitting member) having a horizontal mounting surface (top surface), a cell transfer line 10 assembled on the top surface of the base 1, a camera unit 5 (imaging device) disposed below the base 1, and a head unit 61 which is disposed above the base 1 and to which a tip 6 for suctioning and discharging cells C is to be attached. In FIG. 1, although a plurality of camera units 5 and head units 61 are illustrated, which indicates the positions P11 to P15, P21 to P23 to which the units 5, 61 are to be transferred, a single number of camera unit 5 and head unit 61 is provided to the cell transfer device S0, in actuality. Alternatively, the cell transfer device S0 may be provided with a plurality of units 5 and units 61.

The base 1 has predetermined rigidity and has a rectangular flat plate partly or wholly made of light transmitting material. Preferably, the base 1 is made of a glass plate. Forming the base 1 with the light transmitting material such as glass plate enables the camera unit 5 disposed below the base 1 to image each operation section on the cell transfer line 10 disposed on the top surface of the base 1 through the base 1.

The cell transfer line 10 includes a plurality of operation sections needed for carrying out a consecutive cell transfer process of suctioning a cell C from a single container by a tip 6 and transporting the suctioned cell C to another container to discharge the cell C from the tip 6. The operation sections are arranged in a left-and-right direction with respect to the base 1 and mounted to the base 1. The plurality of operation sections on the cell transfer line 10 includes a tip stock section 11, a tip calibration section 12, a selecting section 13, a transfer section 14, and a tip disposal section 15.

The camera unit 5 includes a lens part 51 and a camera body 52. The lens part 51 is an objective lens used in an optical microscope and includes a lens group forming an optical image of a predetermined magnification and a lens barrel accommodating the lens group. The camera body 52 includes an imaging element such as a CCD image sensor. The lens part 51 forms an optical image of an imaging subject on a light receiving surface of the imaging element. The camera unit 5 can move in a left-and-right direction below the base 1 along a guide rail 53 parallelly extending in the left-and-right direction with respect to the base 1. In addition, the lens part 51 can move in an up-and-down direction for an in-focus operation.

The head unit 61 includes a head body 62 and a plurality of heads 63 that are retained by the head body 62 and are capable of moving in an up-and-down direction with respect to the head body 62. Although FIG. 1 exemplifies three heads 63 arranged in a single row, the heads 63 are not particularly limited in its number and arrangement. The head unit 61 can move in a left-and-right direction (X direction) above the base 1 along the guide rail 64 parallelly extending in the left-and-right direction with respect to the base 1. Note that the head unit 61 can also move in a direction (Y direction) perpendicular to the sheet of FIG. 1, although not illustrated in FIG. 1.

The head 63 is made of a hollow rod having an open lower end. The tip 6 is mounted to the lower end of the head 63. The tip 6 is made of a tapered tubular member and has a tip end opening 6t for suctioning and discharging a cell C (object). A piston mechanism is mounted in the hollow part of the head 63 and the piston mechanism can operate to generate suctioning and discharging force at a lower end opening of the head 63. The head body 62 incorporates a power unit for the piston mechanism, an elevation mechanism for moving the head 63 in the up-and-down direction, and a power unit of the elevation mechanism. Suctioning and discharging force generated in the head 63 generates suctioning and discharging force in the tip end opening 6t of the tip 6 mounted to the head 63. Accordingly, the tip 6 suctions and discharges a cell C through the tip end opening 6t of the tip 6.

[Details of Cell Transfer Line]

Next, each operation section on the cell transfer line 10 will be described. The tip stock section 11 is a part to store a lot of non-used tips 6. Disposed in the tip stock section 11 is a stock container 16 that retains tips 6 arranged in a standing and matrix posture. The tip 6 is retained in the stock container 16 such that an upper end opening of the tip 6 faces upward. Specifically, the tip 6 is retained in the stock container 16 so that it can be easily mounted to a lower end of the head 63 that moves in the up-and-down direction.

The tip calibration section 12 is a part for determining a position (XYZ coordinates) of the tip end opening 6t of the tip 6 mounted to the head 63. The tip calibration section 12 is provided with an imaging pit 17 for imaging, by the camera unit 5, a tip 6 mounted to the head 63. The position of the tip end opening 6t of the tip 6 in the XYZ coordinates is determined based on an image of the tip 6 and focal position information during imaging.

The position in the XYZ coordinates is determined to accurately determine a position of the tip end opening 6t of each tip 6 and accurately determine a transfer amount of the head unit 61 in the XY directions and a transfer amount of the head 63 in the Z direction during suctioning and discharging of the cells C. For example, the height position of the tip end opening 6t varies depending on a mounting error of the tip 6 with respect to the head 63, a dimensional error of the tip 6 itself, and an error in a driving system of the head 63. Imaging of the tip 6 through the tip calibration section 12 determines a deviation of the tip end opening 6t, derived from the errors, with respect to a reference position and a correction value corresponding to the deviation is determined.

The selecting section 13 is a part to select cells C targeted to be transferred. A selecting container 18 (light transmitting container) is disposed in the selecting section 13. The selecting container 18 is a container from which cells C are transferred and which stores culture medium L and retains a cell selecting dish 2 (retaining part) in the state that the dish is immersed in the culture medium L. The dish 2 is a plate to retain cells C and includes a plurality of retaining recesses 3 on a top surface thereof, the recesses each being capable of retaining a cell C individually. The culture medium L can be appropriately selected depending on the type of cells C and is not limited to a particular type as long as the cells C are not deteriorated in their characteristics.

The selecting container 18 has a columnar or prismatic shape and has a rectangular upper surface opening 18H on an upper surface side thereof. The upper surface opening 18H is an opening used for receiving cells C and for the tip 6 mounted to the head 63 to pick up a selected cell C. The dish 2 is arranged below the upper surface opening 18H. The selecting container 18 and the dish 2 used are made of light transmitting resin material or glass. This is for the camera unit 5 disposed below the selecting container 18 to be able to observe the cells C carried in the dish 2.

A plurality of cells C dispersed in the cell culture solution is injected into the selecting container 18 through a dispersing tip not shown. The dispersing tip suctions cells C and cell culture solution from a tube that stores the cell culture solution containing a lot of cells C and retains them inside the dispersing tip. Then, the dispersing tip is moved to a location above the selecting container 18 and is accessed to an upper surface of the dish 2 through the upper surface opening 18H. Subsequently, a tip end opening of the dispersing tip is immersed into the culture medium L of the selecting container 18 to discharge the cells C, together with the cell culture solution, retained inside the tip. The cell transfer device S0 includes the cell stock section in which the tube is disposed and a dispersing tip stock section storing a plurality of dispersing tips, which sections are excluded from FIG. 1.

Figure 2A:
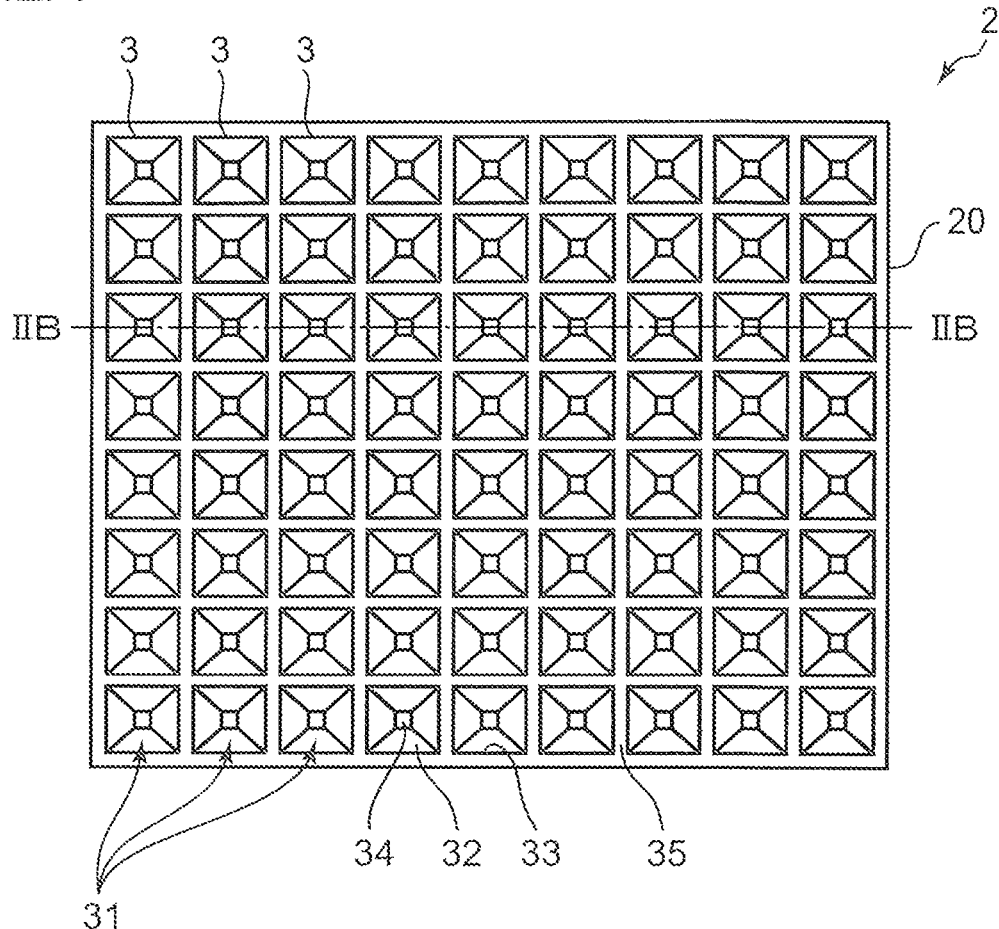
FIG. 2A is a view showing a top surface of a dish provided to a selecting container used in the cell transfer device.
Figure 2B:
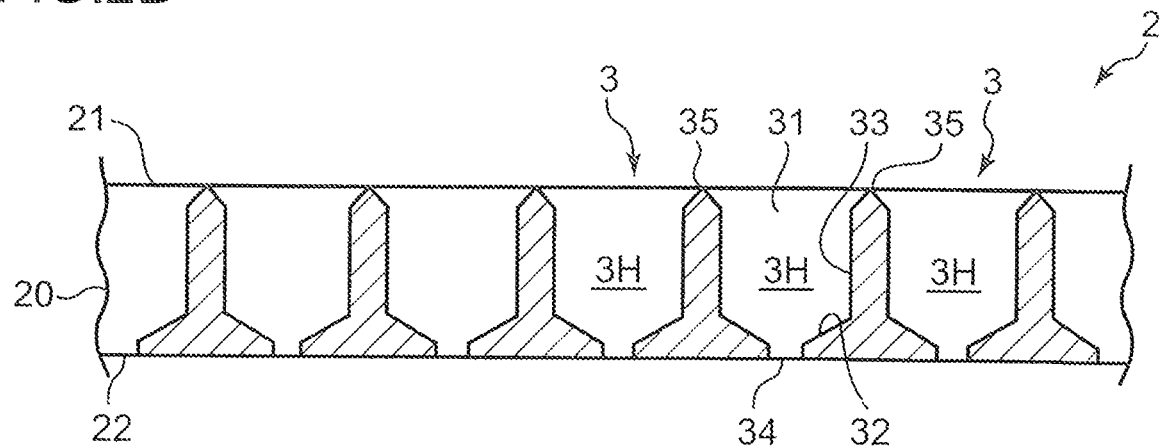
FIG. 2B is a cross section along line IIB-IIB in FIG. 2A.

FIG. 2A is a plan view of the dish 2 and FIG. 2B is a cross section along line IIB-IIB in FIG. 2A. The dish 2 includes a dish body 20 and the retaining recesses 3 formed in the dish body 20. The dish body 20 is made of a flatty plate member having a predetermined thickness and has an upper surface 21 and a lower surface 22. Each retaining recess 3 has an opening (opening 31), at a side of the upper surface 21, for receiving a cell C. The dish 2 is immersed into the culture medium L inside the selecting container 18. More specifically, the dish body 20 is retained inside the selecting container 18 such that the upper surface 21 of the dish body 20 is immersed into the culture medium L inside the selecting container 18 while the lower surface 22 thereof is positioned with a distance with respect to a bottom plate of the selecting container 18 (see FIG. 1).

Each of the retaining recesses 3 has an opening 31, a bottom part 32, a tubular wall surface 33, a hole part 34 and a border part 35. This embodiment shows an example in which square retaining recesses 3 are arranged in a matrix form in a plan view. The opening 31 is a square opening provided to the upper surface 21 and has a size to allow entrance of the tip end opening 6t of the tip 6 for selection. The bottom part 32 resides inside the dish body 20 and is located near the lower surface 22. The bottom part 32 forms an inclined surface gently inclining downward toward the center (the center of the square). The tubular wall surface 33 is a wall surface vertically extending downward from the opening 31 toward the bottom part 32. The hole part 34 is a through hole vertically penetrating between the center of the bottom part 32 and the lower surface 22. The border part 35 is located at the upper surface 21, is an area to become an opening edge of each retaining recess 3 and is a ridgeline partitioning the retaining recesses 3.

A storing space 3H for storing a cell C is partitioned by the bottom part 32 and the tubular wall surface 33 of each retaining recess 3. Generally, the storing space 3H is contemplated to store a single number of cell C. The hole part 34 is provided to discharge a small cell of undesired size or a foreign matter from the storing space 3H. Accordingly, the hole part 34 has a selected size through which a cell C of desired size cannot pass through while a small cell C of undesired size and a foreign matter can pass through. As a result, a cell C to be a target for selection is trapped in the retaining recess 3 while a foreign matter or the like drops on the bottom plate of the selecting container 18 through the hole part 34.

The cell C retained in the retaining recess 3 is suctioned by the tip 6. In this suctioning operation, when the head 63 is moved downward, the tip end opening 6t of the tip 6 enters inside the retaining recess 3 and approaches closer to the cell C swiftly. Then, suction force generated in the tip end opening 6t causes the tip 6 to suction the cell C into an inside thereof. Such operation of the tip 6 requires accurate determination of the height position of the dish 2 (retaining recess 3). It is because an inadequate suctioning operation may occur by insufficient determination of the height position, which can result in a collision of the tip end opening 6t against the bottom part 32 of the retaining recess 3 or can result in an inadequate approach of the tip end opening 6t to the cell C to cause a suctioning failure. The dish 2 is retained in the selecting container 18 at a height position in accordance with a designed value, but a deviation in the height position can sometimes occur due to manufacturing error or the like. According to the present embodiment, a correction value corresponding to such deviation is determined as the selecting container 18 is imaged by the camera unit 5 in the selecting section 13 and a deviation of the height position of the dish 2 with respect to a reference position is determined from image information acquired.

The transfer section 14 is an area to transfer the cells C selected in the selecting section 13. A microplate 4 is arranged in the transfer section 14. The microplate 4 is a container in which cells C are transferred and includes a plurality of wells 41 for receiving the cells C. The tip end opening 6t of the tip 6 in which a cells C is suctioned enters into each well 41 and discharges the cell C. The microplate 4 used is also made of light transmitting resin material or glass. This is for the camera unit 5 disposed below the microplate 4 to be able to observe the cells C carried in the microplate 4.

Accurate determination of the height position of the bottom surface of the well 41 is desirable since the tip end opening 6t of the tip 6 enters into the well 41. Alternatively, a container such as a petri dish may be arranged in the transfer section 14 in place of the microplate 4, in which case accurate determination of the height position of the bottom surface of the container is also desirable. In order to determine these height positions, it is desired that the camera unit 5 images the microplate 4 or petri dish to determine, from the acquired image information, a deviation between the height position of the bottom surface and the reference position to determine a correction value corresponding to the deviation.

The tip disposal section 15 is an area to collect tips 6, used to complete the suctioning and discharging operations, from the head 63. The tip disposal section 15 includes a tip collecting container 19 for storing the used tips 6. In the disposal operation, the head unit 61 mounted with the used tips 6 is transferred above the opening of the tip collecting container 19 and an operation for removing the tips 6 from the head 63 is carried out. With this removing operation, the tips 6 drop into the tip collecting container 19.

[Description of Cell Transfer Operation]

Next, a cell transfer operation by the cell transfer device S0 will be described. The basic steps of the cell transfer operation includes: mounting of the head 63 to the tip 6 (step 1); positional calibration of the tip end opening 6t of the tip 6 (step 2); picking up of a cell C from the selecting container 18 (dish 2) (step 3); transfer of the cell C to the microplate 4 (step 4); and disposal of the tip 6 (step 5). In order to carry out these steps, the head unit 61 is traveled from the left to the right above each section of the cell transfer line 10 along the guide rail 64.

The camera unit 5 images the tip 6 mounted to the head 63 to determine the position of the tip end opening 6t in step 2, images the dish 2 to select usable cells C before step 3, and images the microplate 4 to determine the cells C that have been transferred after step 4. Additionally, the camera unit 5 images the dish 2 to determine the height position thereof and images the microplate 4 or petri dish to determine the height position of the bottom surface thereof, before carrying out steps 1 to 5.

Each of steps 1 to 5 will be described below. In step 1, the head unit 61 is transferred to a tip mounting position P11 above the tip stock section 11. Here, as shown by the dotted line in FIG. 1, one head 63 is aligned with a corresponding tip 6 retained in the stock container 16 and is moved downward to fit an upper end part of the tip 6 to the lower end of the head 63. Then, the head 63 is moved upward. Same operation is carried out for the rest of the heads 63 for attachment of the tips 6.

In order to carry out the subsequent step 2, the head unit 61 is transferred to a tip calibration position P12 above the tip calibration section 12. Here, the head unit 61 is stopped at a location where one head 63 newly mounted with the tip 6 is aligned with the vertical axis of the imaging pit 17. Meanwhile, the camera unit 5 is transferred to a tip imaging position P21 right below the imaging pit 17 of the tip calibration section 12. Then, the camera unit 5 images the tip 6 positioned above the imaging pit 17.

The position of the tip end opening 6t is determined by the contrast detection method, for example. Specifically, the tip 6 is imaged sequentially by the camera unit 5 initiating from a predetermined imaging starting point below the tip end opening 6t while the lens part 51 is shifted upward by several tens of microns. The imaging terminal point is a predetermined location that can be determined as above the tip end opening 6t. The height position of the tip end opening 6t is determined based on the height position of the lens part 51 in which a focal position is determined by an in-focus position where a taken image of a line supposed to be the tip end opening 6t has the highest contrast among the taken images. Thus determined height position is compared with a reference position where the tip 6 is accurately mounted to the head 63 and a correction value is determined by the difference. This correction value is used as a correction value for controlling the transfer of the head unit 61 (head 63). Same images and correction values are determined for the rest of the heads 63.

In step 3, the head unit 61 is transferred to a cell suction position P13 above the selecting section 13. Note that cell suspension containing cells C is distributed in the dish 2 of the selecting container 18 and the cells C are retained in the dish 2 before step 3 is carried out. The camera unit 5 is transferred to a dish imaging position P22 below the selecting section 13 and images the dish 2 carrying the cells C. A usable cell C is determined based on the image acquired and the coordinates of the retaining recess 3 retaining the usable cell C is specified. Then, a suction sequence where which cell C is to be suctioned with which head 63 (tip 6) and in what order is arranged. In addition, a discharge sequence is also arranged in which from, which head 63 (tip 6) to which well 41 of the microplate 4 is subjected to the discharge operation.

Following the arrangement of the suction sequence, a tip 6 for the first suction is aligned with a retaining recess 3 of a dish 2 of suction target and the head 63 is moved downward with reference to the correction value acquired in step 2. After the tip end opening 6t of the tip 6 comes into the culture medium L in the selecting container 18 and resides against the retaining recess 3 of the target, suction force is generated in the head 63. With this, the cell C carried in the retaining recess 3 of the target is suctioned into the tip 6. Then, the head 63 is moved upward. Hereinafter, in accordance with the suction sequence, same operation is carried out sequentially between the succeeding tips 6 and retaining recesses 3 for suction of the cells C into the respective tips 6.

In step 4, the head unit 61 is transferred to a cell discharging position P14 of the transfer section 14, i.e., above the microplate 4. The head unit 61 is stopped so that the tip 6 retaining the cell C is vertically aligned with the well 41 of the microplate 4 that is a discharge target. Then, the head 63 is moved downward until the tip end opening 6t of the tip 6 enters the opening of the well 41. Subsequently, discharge force is generated in the head 63 and the cell C retained inside the tip 6 is discharged from the tip end opening 6t to the well 41. In step 4, the camera unit 5 is transferred to a microplate imaging position P23 below the transfer section 14. The camera unit 5 captures an image of the microplate 4 carrying the cell C after completion of discharge of the cell C into the well 41. Accordingly, carrying condition of the cell C in the microplate 4 can be determined.

In step 5, the head unit 61 is transferred to a tip disposal position P15 above the tip disposal section 15. A tip collecting container 19 having an open upper surface is disposed in the tip disposal section 15. The head 63 is moved downward with respect to the tip collecting container 19 and a tip removing rod (not shown) incorporated inside the head 63 is moved downward. The downward movement of the rod pushes and presses the tip 6, so that the tip 6 is removed from the head 63. The removed tip 6 drops inside the tip collecting container 19.

[Imaging System]

Figure 3:
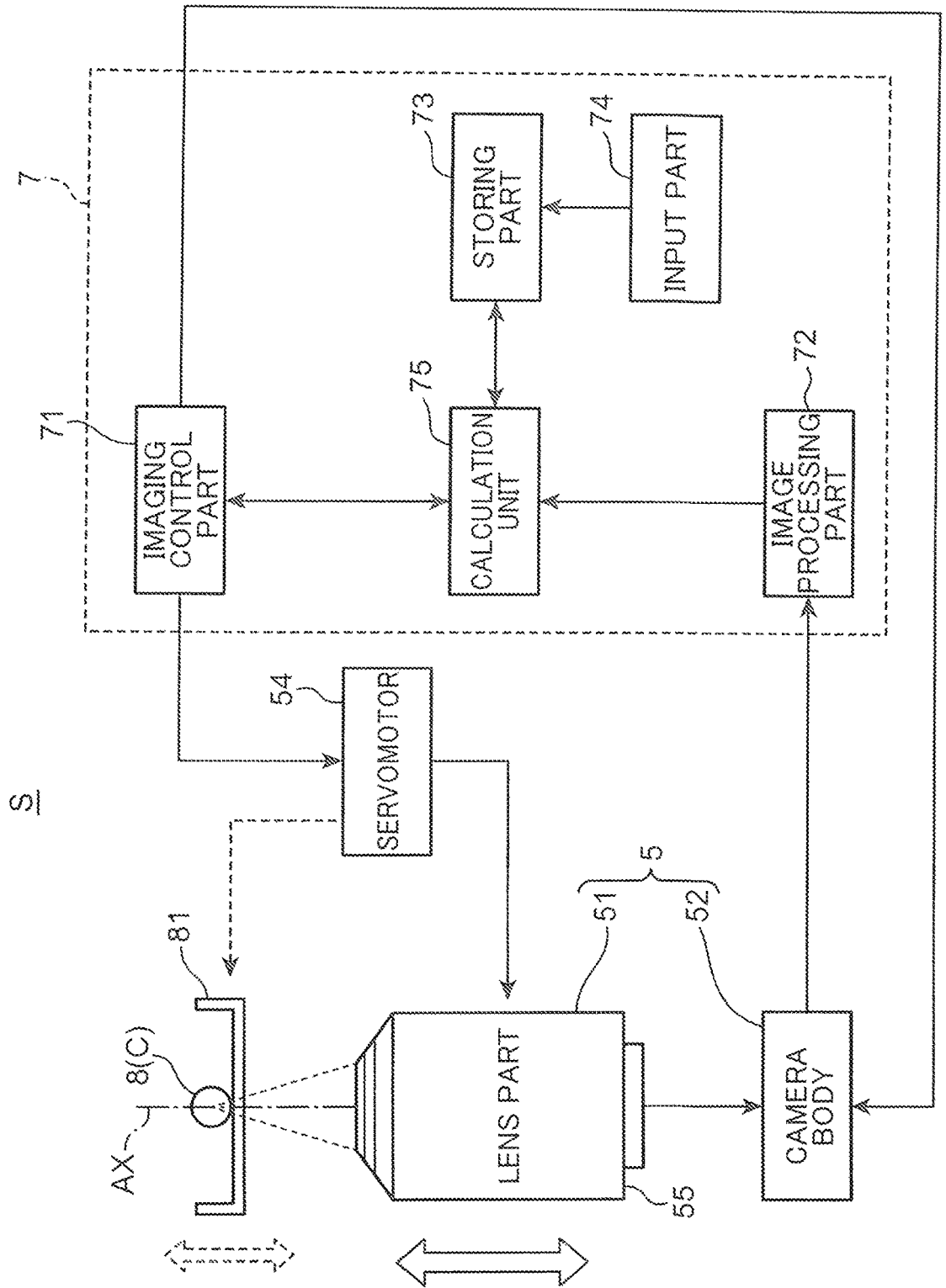
FIG. 3 is a block diagram of an imaging system according to an embodiment of the present disclosure.

Next, with reference to FIG. 3, an imaging system S, including the camera unit 5 described above, according to an embodiment of the present disclosure will be described. The imaging system S includes the camera unit 5 configured to image an imaging subject on an imaging optical axis AX, a controller 7 configured to control operation of the lens part 51 and carry out predetermined process based on image information acquired by the camera body 52, and a servomotor 54 moving the lens part 51 up and down. FIG. 3 illustrates, as an imaging subject, a spherical imaging subject 8 placed on the light transmitting container 81 (light transmitting member). The imaging subject 8 corresponds to a cell C retained in the dish 2 or the microplate 4, for example. Note that in the present embodiment, the imaging subject includes the tip end opening 6t of the tip 6, the dish 2, and the bottom surface of the container, etc.

The servomotor 54 rotates forward or reverse to move the lens part 51 in a up-and-down direction, with the predetermined resolution, via a power transmission mechanism not shown. With this movement, the focal position of the lens part 51 is adjusted to the position of the imaging subject 8. Note that as shown by the dotted line in FIG. 3, the servomotor 54 may be used instead of the lens part 51 to move up and down the light transmitting container 81 or stage on which the light transmitting container 81 is placed.

The controller 7 is composed of a personal computer, for example, and operates a predetermined program to functionally include an imaging control part 71, an image processing part 72, a storing part 73, an input part 74, and a calculation unit 75.

The imaging control part 71 controls operation of the camera unit 5. Specifically, the imaging control part 71 controls an imaging operation (exposure amount and/or shutter timing) of the camera body 52. Furthermore, the imaging control part 71 provides a control pulse to cause the servomotor 54 to move the lens part 51 up and down by a predetermined pitch (several tens of μm pitch, for example). The imaging control part 71 is given from the calculation unit 75 data relating to a regulated height position of the imaging subject 8, i.e., a predetermined position as a height position where the imaging subject 8 is supposed to be positioned. Designating the regulated height position as a target position, the imaging control part 71 instructs the servomotor 54 to cause the lens part 51 to move to the target position. Data relating to the position that the imaging control part 71 has instructed is input to the calculation unit 75. In addition, the imaging control part 71 causes the camera body 52 to capture an image of the imaging subject 8 for every movement pitch of the lens part 51.

The image processing part 72 performs predetermined image processing on image data of the imaging subject 8 acquired by the camera body 52. The image processing part 72 performs image processing such as edge detection processing and pattern recognition processing involving feature amount extraction on the image data, etc., to provide processing to extract the shape of the imaging subject 8 from the image data. Furthermore, the image processing part 72 determines contrast between pixels for each image data acquired for every movement pitch of the lens part 51 and specifies an image having greatest contrast as an in-focus image. The height position data of the lens part 51 when the in-focus image is acquired is provided to the calculation unit 75.

The storing part 73 stores various data. The stored data includes a reference height of the lens part 51 as a part of the data. The reference height is a height position of a torso surface 55 of the lens part 51 determined on the basis of the regulated height position of the imaging subject 8 and a parfocal distance of the lens part 51. In this embodiment, as will be described in detail later, the reference height is corrected corresponding to the focal extension amount when a light transmitting member such as the light transmitting container 81 is interposed on the imaging optical axis AX. When the size of the imaging subject 8 changes by the interposition of the light transmitting member, the storing part 73 stores the data relating to a change rate of the size as a part of the data.

The input part 74 receives from a user input of data relating to the reference height determined from the parfocal distance and the corrected reference height acquired from a theoretical value or actual measurement of the focal extension amount, and input of data relating to the change rate of the size.

In addition, the storing part 73 stores as a correction value the difference between the reference height (or the corrected reference height) and the actually measured height objected by actual imaging of the imaging subject 8 performed by the camera unit 5. Furthermore, when the tip end opening 6*t* of the tip 6 and the bottom surface of the dish 2 or the container is regarded as an imaging subject, correction values of these are also stored in the storing part 73. These correction values are applied to control movement of the head 63 (tip 6).

The calculation unit 75 determines data relating to the position and/or the size of the imaging subject 8 based on image information acquired from images captured by the camera unit 5. Specifically, the calculation unit 75 reads out the reference height data value from the storing part 73 when data relating to the position of the imaging subject 8 is to be determined. In addition, the calculation unit 75 acquires data relating to the actually measured height of the lens part 51 when an in-focus image is acquired from the image processing part 72. Then, a correction value about the height position of the imaging subject 8 is determined by the comparison between the reference height data and the data relating to the actually measured height. That is, a deviation amount between the theoretical height position of the imaging subject 8 and the actual height position is determined.

As shown in FIG. 3, the calculation unit 75 acquires change information relating to a condition change in an imaging caused by the interposition of the light transmitting container 81 when the light transmitting container 81 is interposed on the imaging optical axis AX in the imaging. When the position of the imaging subject 8 is to be determined, the change information is a focal extension amount, for example, and in this case, the calculation unit 75 reads out from the storing part 73 the reference height data value corrected based on the focal extension amount. Then, the calculation unit 75 determines a correction value about the height position of the imaging subject 8 by comparing the corrected reference height data with the data relating to the actually measured height. As a result, it is contemplated that the height position data of the imaging subject 8 is corrected based on the change information (focal extension amount).

When data relating to the size of the imaging subject 8 is to be determined, the calculation unit 75 calculates shape data indicating the sizes of X, Y, and Z of the imaging subject 8 based on an in-focus image selected by the image processing part 72. In addition, when the light transmitting container 81 is interposed on the imaging optical axis AX in the imaging, the calculation unit 75 acquires change information relating to the change in the image of the imaging subject 8 caused by the interposition of the light transmitting container 81. Specifically, a change rate of the size of the imaging subject 8 stored in the storing part 73 in advance is read out. This change rate is a change rate between the actual size of the imaging subject 8 and a size in the image of the imaging subject 8 acquired by the camera unit 5 with the light transmitting container 81 (light transmitting member) being interposed. The calculation unit 75 corrects the shape data with reference to the change rate.

[About Focal Extension Amount]

Figure 4:
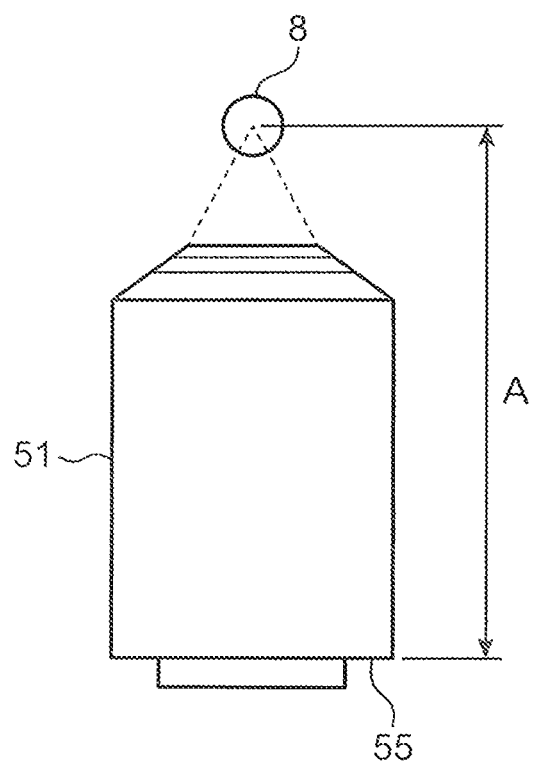
FIG. 4 is a view for describing a parfocal distance of a lens part.

Now, the focal extension amount will be described referring to FIGS. 4 to 6. FIG. 4 is a view for describing the parfocal distance of the lens part 51. A focal position of the lens part 51, which is an objective lens, configured to image minute subjects such as cells C, is determined by the parfocal distance A from the torso surface 55. Thus, the distance between the imaging subject 8 and the torso surface 55 becomes the parfocal distance A when the imaging subject 8 is in an in-focus state. Accordingly, it becomes possible to measure the height position of the imaging subject 8 based on the height position of the torso surface 55 as a reference height.

Figure 5:
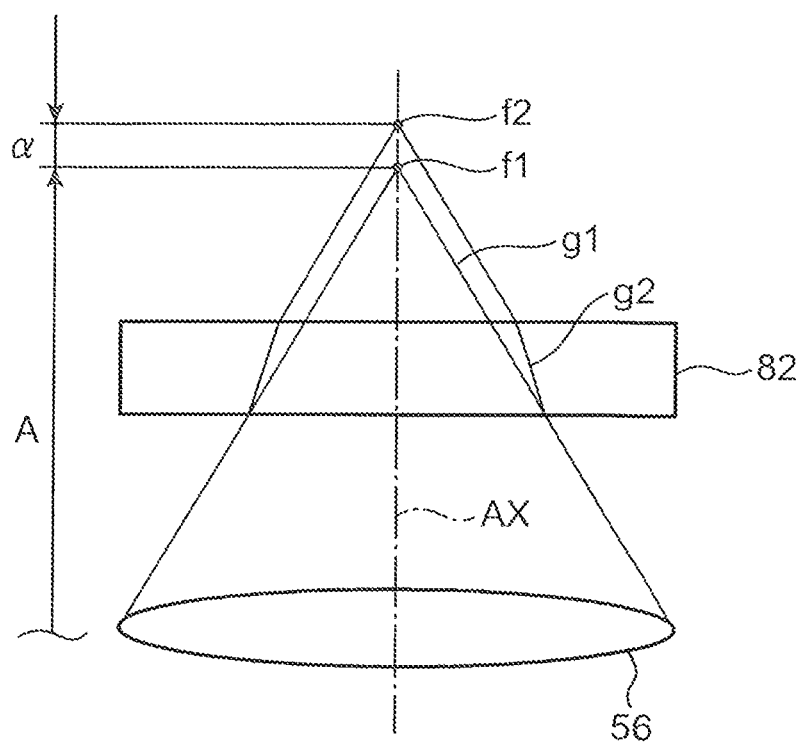
FIG. 5 is a view for describing a focal extension amount.

FIG. 5 is a view for describing the focal extension amount α. The focal position of the lens part 51 extends further when the light transmitting member 82 is interposed on the imaging optical axis AX of the lens part 51. That is, when the light transmitting member 82 is not interposed, a light beam g1 passed through a lens 56 of the lens part 51 forms an image on the focal position f1 defined by the shape of the lens. In contrast, when the light transmitting member 82 is interposed, an optical path refracts in accordance with the refractive index of the light transmitting member 82. Thus, the light beam g2 passing through the light transmitting member 82 forms an image on the focal position f2 that is further than the focal position f1. The distance between the focal positions f1, f2 on the imaging optical axis AX is the focal extension amount α (change information).

When the light transmitting member 82 is interposed on the imaging optical axis AX, the distance between the imaging subject 8 and the torso surface 55 becomes a distance obtained by adding the focal extension amount α to the parfocal distance A. Thus, it becomes possible to accurately measure the height position of the imaging subject 8 by determining the focal extension amount α in advance and by setting the height position of the torso surface 55 as the height position corrected by the focal extension amount α, even when the light transmitting member 82 is interposed.

Figure 6:
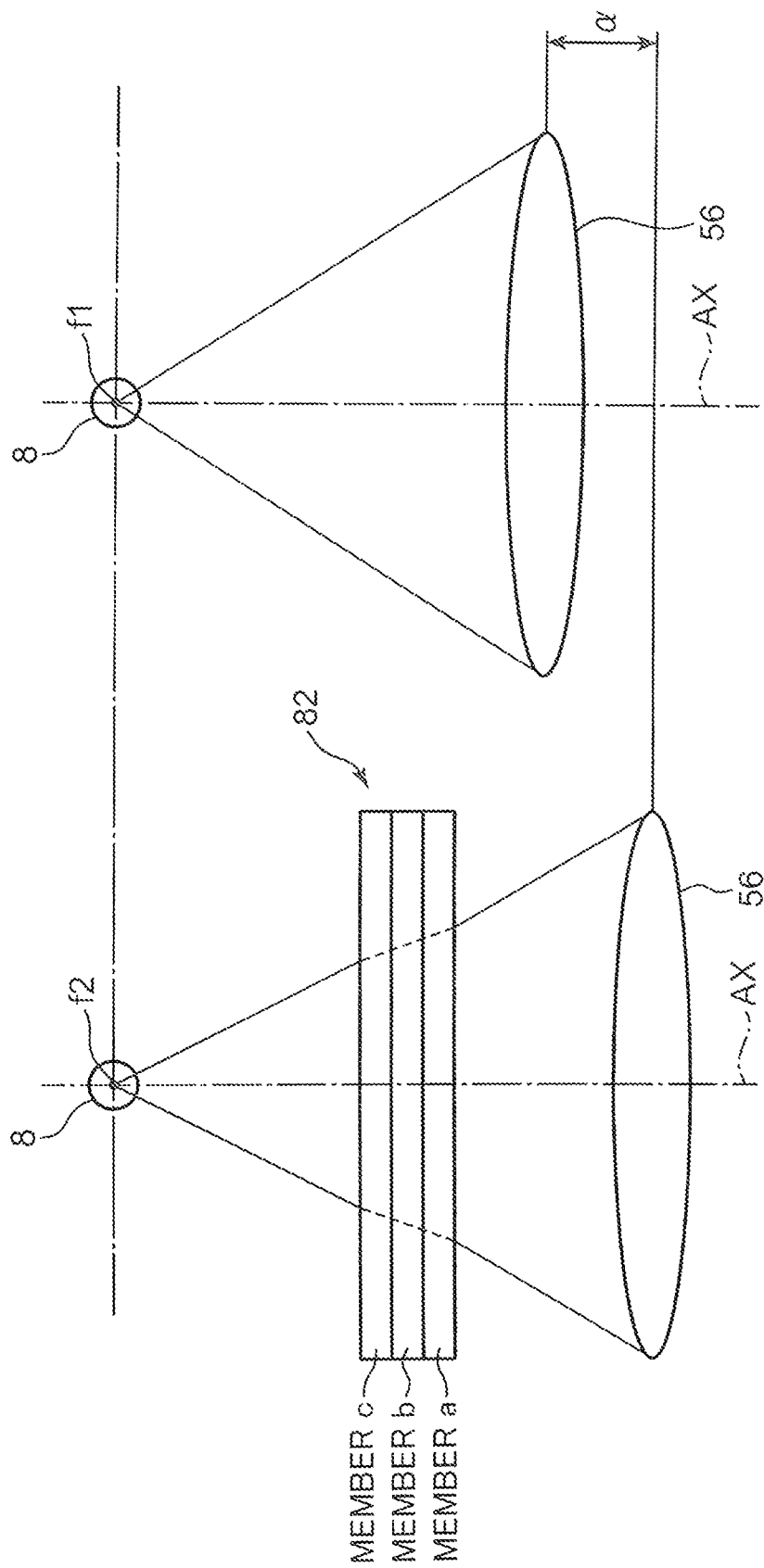
FIG. 6 is a view for describing a method for measuring the focal extension amount when a light transmitting member is interposed on an imaging optical axis.

FIG. 6 is a view for describing a method for measuring the focal extension amount α when the light transmitting member 82 is interposed on the imaging optical axis AX. The light transmitting member 82 interposed on the imaging optical axis AX is made of a single type of member, so that the focal extension amount a can be calculated based on the Snell's Law if the refractive index thereof is known. In this instance, the storing part 73 is used to store via the input part 74 the corrected reference height in which the reference height, which is the height position of the torso surface 55 in focusing the imaging subject 8, is added with the focal extension amount α determined by the calculation.

However, it is difficult to determine by calculation the focal extension amount α if the light transmitting member 82 is made of a plurality of types of members. The light transmitting member 82 in FIG. 6 is an example that is a combined composition of different members a, b, c. In the embodiment, when a cell C retained in the dish 2 is to be imaged, for example, the base 1, the selecting container 18 and the culture medium L are to be interposed on the imaging optical axis AX. In such a case, it is difficult to calculate the focal extension amount α of the combined composition even if the refractive index of each member is known. Thus, it is desirable to determine the focal extension amount α by actual measurement of the focal position f2 using the imaging system S.

In this case, as schematically illustrated in FIG. 6, the lens part 51 takes an in-focus operation for a case in which the light transmitting member 82 is interposed on the imaging optical axis AX and for a case the member 82 is not interposed on the axis AX, while the imaging subject 8 is placed on the same height position for both cases. More specifically, first, the imaging control part 71 moves the lens part 51 to an in-focus position for a case the light transmitting member 82 is not interposed. That is, the imaging control part 71 moves the lens part 51 so that the height position of the torso surface 55 with respect to the imaging subject 8 becomes the parfocal distance A. The height position of the torso surface 55 after it is moved is determined as the reference height. Note that the parfocal distance A of the lens part 51 is generally known by the specification of the lens part 51, so that a movement amount in accordance with the specification is to be set. Obviously, the torso surface 55 can be set as the reference height by imaging with the light transmitting member 82 excluded from the imaging optical axis AX and by allowing the image processing part 72 to select the in-focus position using the contrast detection system.

Then, the imaging control part 71 causes the camera unit 5 to image the imaging subject 8 for a plurality of times while a relative distance with respect to the imaging subject 8 is changed and while the light transmitting member 82 is interposed on the imaging optical axis AX. In an example in FIG. 6, while the imaging control part 71 moves the lens part 51 gradually in the direction away from the imaging subject 8 at a predetermined pitch, the camera body 52 captures an image of the imaging subject 8 for every pitch. Then, the image processing part 72 selects the in-focus position using the contrast detection system. Thereafter, the calculation unit 75 calculates the focal extension amount α for the imaging subject 8 based on the image information acquired by the plurality of imaging operations. More specifically, the calculation unit 75 calculates the focal extension amount α from the difference between the height position of the torso surface 55 with the light transmitting member 82 not being interposed and the height position of the torso surface 55 with the in-focus image being acquired while the light transmitting member 82 is interposed.

Exemplified applications of the cell transfer device S0, in the imaging system S, for respective sections will be described below.

[First Exemplified Application]

Figure 7:
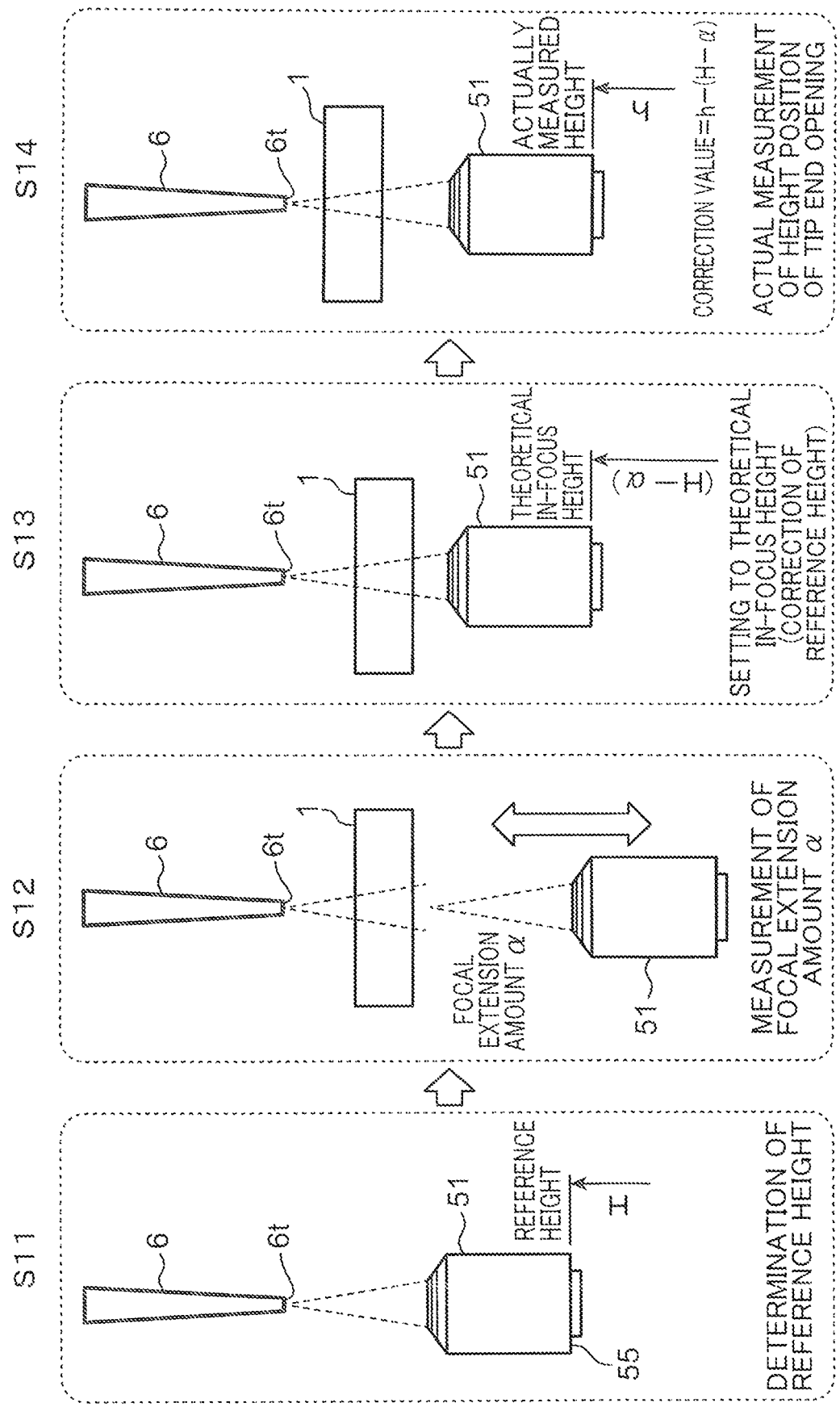
FIG. 7 is a view showing a first exemplified application of the imaging system.

FIG. 7 is a view illustrating a first exemplified application of the imaging system S. The first exemplified application demonstrates an example where the imaging subject is the tip 6 mounted to the head 63 and the height position of the tip end opening 6t of the tip 6 is measured. First, as shown in step S11, the reference height H is determined by the height position of the torso surface 55 in the state that the lens part 51 is focused with respect to the tip end opening 6t of the tip 6 for test. The imaging control part 71 controls the servomotor 54 to locate the torso surface 55 of the lens part 51 to be aligned with the reference height H. The value of the reference height H is stored in the storing part 73.

Then, as shown in step S12, the imaging system S is used to measure the focal extension amount α. As described hereinbefore, the camera unit 5 of the cell transfer device S0 of the present embodiment images the tip end opening 6t of the tip 6 via the transparent base 1 at the tip imaging position P21 right below the imaging pit 17. That is, the imaging control part 71 causes the camera unit 5 to image a zone including at least the tip end opening 6t of the tip 6 for a plurality of times while a vertical relative distance with respect to the test tip 6 is changed and while the base 1 is interposed in the imaging optical axis AX. Alternatively, a dummy tip or the like positioned at a regulated height may be imaged.

By virtue of the interposition of the base 1, the in-focus position of the lens part 51 moves away. Thus, the imaging control part 71 causes the lens part 51 to move gradually in the direction away from the tip 6 at a predetermined pitch, and causes the camera body 52 to capture an image of the tip 6 for every pitch. The image processing part 72 selects the in-focus position from the images of the tip 6 acquired in the pitches, using the contrast detection system. The calculation unit 75 calculates the focal extension amount α from the difference between the reference height H and the height position of the torso surface 55 while the base 1 is interposed and the in-focus image is taken. In this case, (H−α) is the corrected reference height position, i.e., the theoretical in-focus height. Note that the minus mark in (H−α) means that the lens part 51 is moved downward as the focal position moves away. The tip end opening 6t is in-focused at the corrected reference height position (H−α) when the head 63 is moved downward with a regular movement amount while the tip of regular size is mounted to the head 63 regularly.

Then, as shown in step S13, the value of (H−α) acquired is stored in the storing part 73 through the input part 74 by the user. The calculation unit 75 reads out the value of (H−α) from the storing part 73 and provides the imaging control part 71 with the data as a movement target position for the lens part 51. Then, the head 63 mounted with the tip 6 to be measured is moved downward to a predetermined height position. The imaging control part 71 performs servo control on the servomotor 54 based on the movement target position to move the torso surface 55 to the position of the theoretical in-focus height (H−α) while the imaging optical axis AX of the lens part 51 is aligned with the tip 6 to be measured.

Then, as shown in step S14, the actual height position of the tip end opening 6t is determined by the contrast detection system. Specifically, the imaging control part 71 causes the lens part 51 to move in the up-and-down direction at a predetermined pitch based on the position of (H−α) and causes the camera body 52 to capture an image of the tip 6 for every pitch. Thereafter, the image processing part 72 selects the in-focus position by the contrast detection system. The height position of the torso surface 55 at the in-focus position is determined as the actually measured height h corresponding to the actual height position of the tip end opening 6t. The calculation unit 75 determines the correction value for elevation control of the tip 6 (head 63) to be measured based on the actually measured height h and the theoretical in-focus height (H−α).

More specifically, the calculation unit 75 determines the correction value for the tip 6 to be measured based on the following formula:

Correction value=$h-(H-\alpha)$.

For the rest of the tips 6 mounted to the head 63, the operations of steps S13, S14 are repeated and a correction value for each tip 6 is determined in the same manner. The determined correction value is stored in the storing part 73 and referred to at the time of elevation control of the head 63.

[Second Exemplified Application]

Figure 8:
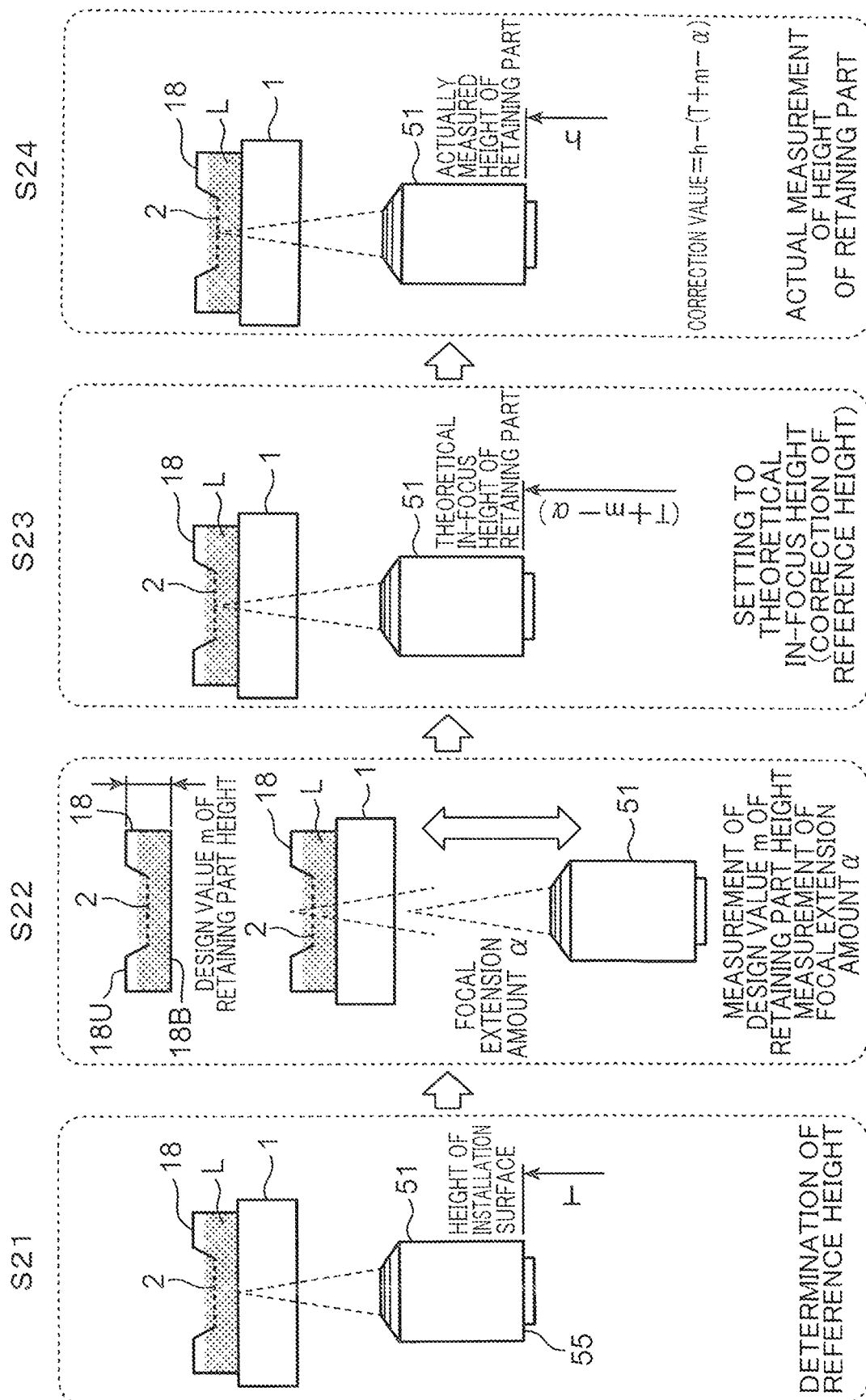
FIG. 8 is a view showing a second exemplified application of the imaging system.

FIG. 8 is a view illustrating a second exemplified application of the imaging system S. The second exemplified application demonstrates an example where the imaging subject is the dish 2 retained in the selecting container 18 and the height position of the dish 2 is measured. First, as shown in step S21, the reference height T is set to the upper surface of the base 1, on which the selecting container 18 is placed, at a location on which the lens part 51 is in-focused. The imaging control part 71 controls the servomotor 54 to place the torso surface 55 of the lens part 51 to the reference height T. The value of the reference height T is stored in the storing part 73. The reference height T is a value that already includes a focal extension amount of the base 1.

Then, as shown in step S22, the imaging system S is used to measure the focal extension amount α. The selecting container 18 has an upper surface 18U (first surface) and a rear surface 18B (second surface) and the dish 2 (retaining part) is placed on the side of the upper surface 18U. In the cell transfer device S0 according to the present embodiment, the camera unit 5 images the dish 2 from the side of the rear surface 18B of the selecting container 18 via the transparent base 1 at a dish imaging position P22 below the selecting section 13.

The reference height T determined in step S21 is the height of the upper surface of the base 1, i.e., the height of the rear surface 18B of the selecting container 18. The dish 2 is located at a higher position apart from the rear surface 18B (bottom wall) of the selecting container 18. Thus, the design value m of the location height of the dish 2 is acquired in advance and the reference height T in step S21 is corrected to (T+m).

Culture medium L is injected into the selecting container 18 placed on the base 1 so that the dish 2 is immersed in the culture medium L for measurement of the focal extension amount α. That is, the light transmitting member in this exemplified application is the bottom wall of the selecting container 18 and the culture medium L. Then, the imaging control part 71 causes the camera unit 5 to image a zone including at least the dish 2 in the selecting container 18 for a plurality of times while the vertical relative distance with respect to the selecting container 18 is changed and while the base 1, the selecting container 18 and the culture medium L are interposed on the imaging optical axis AX. In other words, the imaging control part 71 causes the lens part 51 to move gradually in the direction away from and closer to the selecting container 18 at a predetermined pitch and causes the camera body 52 to capture an image of the selecting container 18 for every pitch.

The image processing part 72 selects the in-focus position of the dish 2 from the images of the selecting container 18 acquired in the pitches, using the contrast detection system. The dish 2 has a thickness in the vertical direction, so that an appropriate location is selected as the focal position. For example, the border part 35 of the dish 2 is a ridgeline sectioning the retaining recesses 3 and is readily detected as an edge on the image, and thus the border part 35 is desirably selected as the focal position.

The calculation unit 75 calculates the focal extension amount α from the difference between the reference height (T+m) and the height position of the torso surface 55 in a condition that the in-focus image is acquired while the selecting container 18 is interposed. In this case, (T+m−α) is the corrected reference height position, i.e., the theoretical in-focus height with respect to the dish 2.

Then, as shown in step S23, the acquired value of (T+m−α) is stored in the storing part 73 from the input part 74 by the user. The calculation unit 75 reads out the value of (T+m−α) from the storing part 73 and provides the imaging control part 71 with the data as a movement target position for the lens part 51. Then, the selecting container 18 retaining the dish 2 to be measured is placed on the base 1. The imaging control part 71 performs servo control on the servomotor 54 based on the movement target position to move the torso surface 55 to the position of (T+m−α) that is the theoretical in-focus height, in a condition that the imaging optical axis AX of the lens part 51 is aligned with the dish 2 to be measured.

Next, as shown in step S24, the actual height position of the dish 2 is actually measured by the contrast detection system. Specifically, the imaging control part 71 causes the lens part 51 to move in the up-and-down direction based on the position of (T+m−α) at a predetermined pitch and causes the camera body 52 to capture an image of the dish 2 immersed in the culture medium L in the selecting container 18 for every pitch. Then, the image processing part 72 selects the in-focus position by the contrast detection system. The height position of the torso surface 55 in the in-focus position is determined as the actually measured height h that corresponds to the actual height position of the dish 2.

The calculation unit 75 determines a correction value to be used in elevation control of the head 63 with respect to the dish 2 based on the actually measured height h and the theoretical in-focus height (T+m−α). The calculation unit 75 determines a correction value for the height position of the dish 2 based on the formula below:

Correction value=$h-(T+m-\alpha)$.

The determined correction value is stored in the storing part 73.

As shown in FIG. 2, the dish 2 is a thin platy member having a predetermined size of vertical times horizontal. Thus, the dish 2 can have tilt and/or warp or can have a thickness variation in the direction of the plate surface. Consequently, an accurate correction value for all of the retaining recesses 3 might not be determined by a mere actual measurement of the position of a single retaining recess 3 in step S24. For this instance, a border part 35 surrounding a single retaining recess 3 should not be determined as the focal position and desirably border parts 35 for a plurality of retaining recesses 3 are determined as the focal position. For example, the border parts 35 of the retaining recesses 3 at four corners of the dish 2 or the retaining recess 3 in the center of the dish 2 are actually measured in step S24 to determine the respective correction values. For the remaining retaining recesses 3, the inclination trend of Lite dish 2 is acquired from the five correction values determined by the actual measurement and the respective correction values can be determined by complementary calculations.

[Third Exemplified Application]

Figure 9:
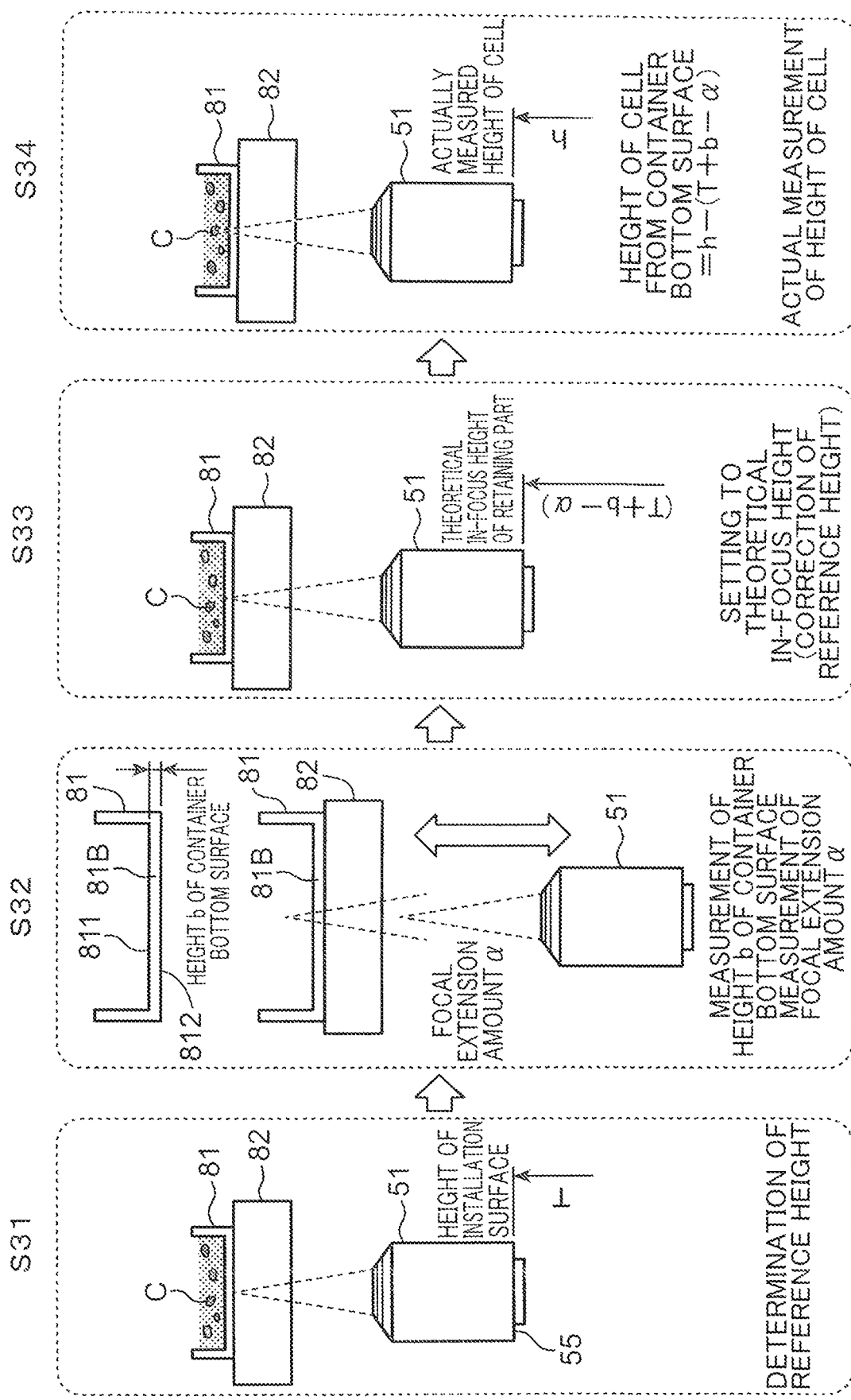
FIG. 9 is a view showing a third exemplified application of the imaging system.

FIG. 9 is a view showing a third exemplified application of the imaging system S. The third exemplified application demonstrates an example where the imaging subject is the cell C retained in the light transmitting container 81 such as a petri dish and the height positions of the cell C is measured. First, as shown in step S31, the reference height T is set to the upper surface of the light transmitting member 82 (or may be the base 1 in the cell transfer device S0), on which the light transmitting container 81 is placed, at a location on which the lens part 51 is in-focused. The imaging control part 71 controls the servomotor 54 to place the torso surface 55 of the lens part 51 to the reference height T. The value of the reference height T is stored in the storing part 73. The reference height T is a value already including the focal extension amount of the light transmitting member 82.

Then, as shown in step S32, the imaging system S is used to measure the focal extension amount $\alpha$. The light transmitting container 81 has an open upper surface and a bottom wall 81B. The camera unit 5 images the cell C through the bottom wall 81B of the light transmitting container 81 via the light transmitting member 82 at a dish imaging position P22 below the selecting section 13.

The reference height T determined in step S31 is the height of the upper surface of the light transmitting member 82, i.e., the height of the bottom wall lower surface 812 of the light transmitting container 81. On the other hand, the surface that the cell C makes a contact is the bottom wall upper surface 811 of the bottom wall 81B (retaining part), i.e., the bottom surface of the container. Thus, the thickness of the bottom wall 81B, i.e., the height b of the bottom wall upper surface 811, is determined by a design value or actual measurement and the reference height T in step S31 is corrected to (T+b).

For measurement of the focal extension amount $\alpha$, the imaging control part 71 causes the camera unit 5 to image a zone including the bottom wall 81B of the light transmitting container 81 for a plurality of times in the state that the vertical relative distance with respect to the light transmitting container 81 is changed while the light transmitting container 81 and the light transmitting member 82 are interposed on the imaging optical axis AX. Specifically, the imaging control part 71 causes the lens part 51 to move gradually in the direction away from and closer to the light transmitting container 81 at a predetermined pitch and causes the camera body 52 to capture an image of the light transmitting container 81 for every pitch. The image processing part 72 selects the in-focus position of the bottom wall upper surface 811 from the images of the light transmitting container 81 acquired in the pitches, using the contrast detection system.

The calculation unit 75 calculates the focal extension amount $\alpha$ from the difference between the reference height (T+b) and the height position of the torso surface 55 in the state that the in-focus image of the bottom wall upper surface 811 is determined. In this case, (T+b−$\alpha$) is the corrected reference height position, i.e., the theoretical in-focus height of the bottom wall upper surface 811, to which the cell C contacts.

Then, as shown in step S33, the acquired value (T+b−$\alpha$) is stored in the storing part 73 from the input part 74 by the user. The calculation unit 75 reads out the value (T+b−$\alpha$) from the storing part 73 and provides the imaging control part 71 with the data as a movement target position for the lens part 51. Thereafter, the light transmitting container 81 accommodating the cell C to be measured is placed on the light transmitting member 82. The imaging control part 71 performs servo control on the servomotor 54 based on the movement target position to move the torso surface 55 to the position (T+b−$\alpha$) that is the theoretical in-focus height, while the imaging optical axis AX of the lens part 51 is aligned with the light transmitting container 81 to be measured.

Next, as shown in step S34, the height position of each of the cells C accommodated in the light transmitting container 81 is measured by the contrast detection system. Specifically, the imaging control part 71 causes the lens part 51 to move in the up-and-down direction based on the position of (T+b−$\alpha$) at a predetermined pitch and causes the camera body 52 to capture an image of the cell C to be imaged in each pitch. Then, the image processing part 72 selects the in-focus position by the contrast detection system. The height position of the torso surface 55 in the in-focus position is determined as the height h of the cell C to be imaged.

The calculation unit 75 determines the correction value of the height position of the cell C based on the actually measured height h and the theoretical in-focus height (T+b−$\alpha$). That is, the correction value indicating how much the cell C is positioned above the bottom wall upper surface 811 is calculated. The calculation unit 75 determines the correction value of the height position of the cell C based on the following formula:

Correction value=$h-(T+b-\alpha)$.

The determined correction value is stored in the storing part 73. The height positions of the rest of the cells C accommodated in the light transmitting container 81 are determined by the same manner. These correction values are used to pick up the cells C from the light transmitting container 81, etc.

[Fourth Exemplified Application]

Figure 10:
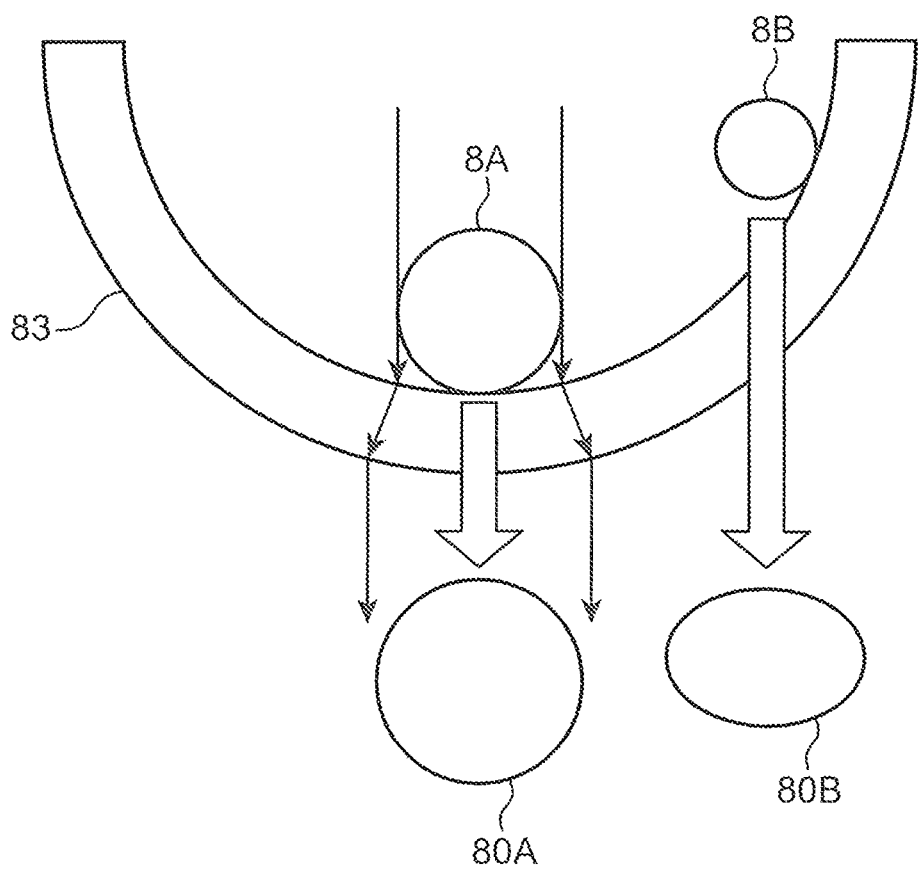
FIG. 10 is a view showing a fourth exemplified application of the imaging system in which a deformation of an imaging subject on the image is shown in the case the imaging subject is imaged through a light transmitting member having a curved surface.
Figure 11:
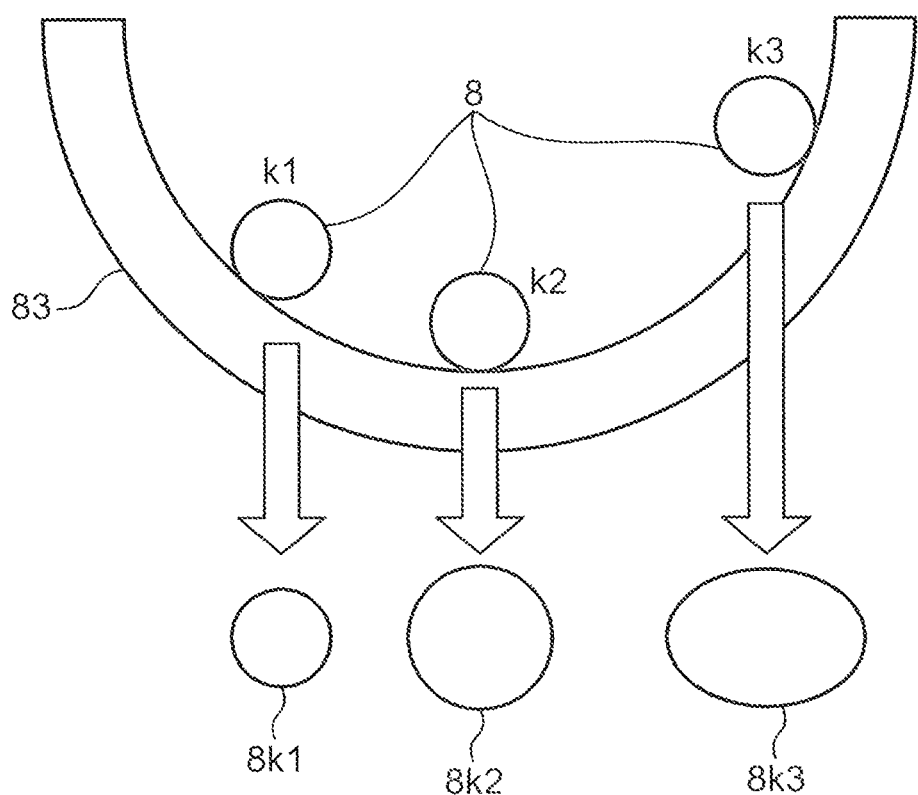
FIG. 11 is a view showing a deformed imaging subject on the image at each retaining position when the imaging subject is imaged through a light transmitting member having a curved surface.
Figure 12:
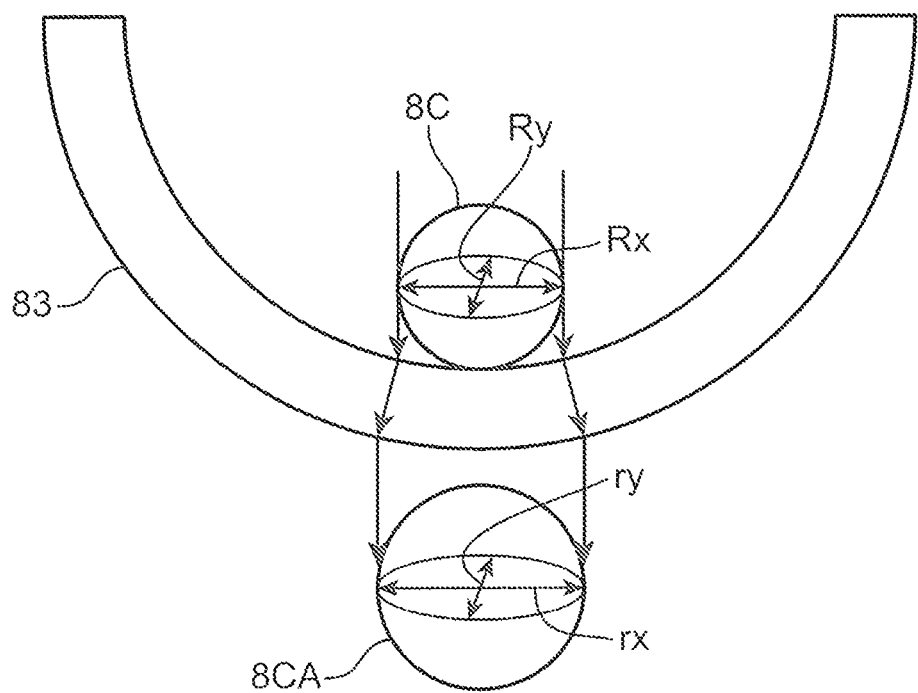
FIG. 12 is a view for describing a change rate of a size of an imaging subject.

FIGS. 10 to 12 are views for describing a fourth exemplified application of the imaging system S. The fourth exemplified application demonstrates an example where the imaging subject to be imaged via a light transmitting member having an optical effect to deform the light image can be imaged so that its size is accurately determined. That is, the fourth exemplified application demonstrates an example where the calculation unit 75 determines data relating to the size of the imaging subject based on the image information acquired by the camera unit 5.

FIG. 10 is a view showing the imaging subjects 8A, 8B deformed on the image when the imaging subjects 8A, 8B are imaged through the light transmitting member having the optical effect described above. Here, the light transmitting member is made of a semispherical transparent curved member 83, as an example. The transparent curved member 83 has a semispherical bottom wall included in the well 41, for example, and the upper surface (first surface) thereof is a retaining part to retain the imaging subjects 8A, 8B and the lower surface (second surface) thereof is a surface through which the camera unit 5 take images. The imaging subjects 8A, 8B are each in contact with the upper surface side of the transparent curved member 83 in which the imaging subject 8A is in contact with the deepest part of the transparent curved member 83 and the imaging subject 8B is in contact with the side surface of the transparent curved member 83. Note that the transparent curved member 83 may have a cone or pyramid shape.

The transparent curved member 83 has a semispherical shape at a lower side thereof, so that it has a lens effect to magnify a light image. Thus, the imaging subjects 8A, 8B are imaged as the imaging subjects 80A, 80B each having a magnified size when the imaging subjects 8A, 8B are imaged from the lower surface side of the transparent curved member 83. In addition, the imaging subjects 8A, 8B may each have a magnified size of different aspect depending on the location on the surface of the transparent curved member 83 with which the subjects 8A, 8B are in contact. For example, the imaging subject 8A positioned on the deepest part of the transparent curved member 83 forms an isotropic size change since that part is the center of the surface having a lens effect, while the imaging subject 8B forms an anisotropy size change since it is located on the position near the end edge of the surface having the lens effect.

Accordingly, the imaging subjects 8A, 8B are imaged as the imaging subjects 80A, 80B with the size on the image deformed from the actual sizes when the imaging subjects 8A, 8B are imaged via the transparent curved member 83 having the lens effect. Fortunately, data having an accurate size of the imaging subjects 8A, 8B can be acquired in such a manner that the aspect of size change, i.e., the change rate of the size (change information), is measured and acquired in advance and the image data of the imaging subjects 80A, 80B acquired by the imaging is corrected based on the change information.

FIG. 11 is a view showing the size change on the image for each retaining positions k1, k2, k3 when the imaging subjects 8 are imaged through the transparent curved member 83. For the measurement of the size change rate, as described with reference to FIG. 10, the aspect of the size change can differ depending on the retaining location on the transparent curved member 83 where the imaging subjects 8 are positioned, so that it is desirable to measure the size change rate with the imaging subjects 8 located in different positions. Specifically, the imaging subjects 8 are located on the respective retaining positions k1, k2, k3 on the upper surface side of the transparent curved member 83 and are imaged from the lower surface side of the transparent curved member 83 to acquire the imaging subjects 8k1, 8k2, 8k3 on the respective positions, from which what size change has formed in each subject can be desirably determined.

FIG. 12 is a view for describing the method to acquire the change rate of the size of the imaging subject 8. For the measurement of the size change rate, the imaging control part 71 causes the camera unit 5 to image at least a zone where a test subject 8C with a known size is retained on the transparent curved member 83 with a predetermined distance with respect to the transparent curved member 83 while the test subject 8C is retained by the transparent curved member 83 on the imaging optical axis. The sizes Rx and Ry of the test subject 8C in the x and y directions are known. In addition, the sizes rx and ry in the x and y directions of the test subject 8CA imaged via the transparent curved member 83 deform with respect to Rx and Ry depending on the refractive index and surface shape of the transparent curved member 83.

The calculation unit 75 calculates the size change rate by the comparison between the size of the test subject 8CA determined based on the image acquired by the imaging and the actual known size of the test subject 8C. Specifically, the calculation unit 75 determines the size change rates in the XY directions based on the following formulas:

the change rate in the $X$ direction=$rx/Rx$; the change rate in the $Y$ direction=$ry/Ry$.

Although FIG. 12 exemplifies that the size change rate for the retaining position k2 in FIG. 11 is determined, the calculation unit 75 is able to determine the size change rates for the retaining positions k1, k3 and additionally retaining positions other than the retaining positions k1 to k3, if necessary, in the same manner. The size change rates acquired are stored in the storing part 73. These size change rates each are applied to correct the size corresponding to the retaining position of the imaging subject 8 when the captured size of the imaging subject 8 retained in the transparent curved member 83 is determined.

According to the fourth exemplified application, it becomes possible to determine how the size has changed as the optical path actually passes through the container (transparent curved member 83) having the lens effect by the comparison between the size of the test subject 8CA determined based on the image acquired by the imaging and the known size of the test subject 8C. Thus, the size change rate can be determined swiftly and accurately, and an additional cost for acquiring the size change rate can be avoided as the imaging system S is used. In addition, it is possible to correct size data corresponding to each retaining position as the size change rate is determined for each retaining position for the test subject 8C.

According to the imaging system S of the present disclosure described above, the calculation unit 75 acquires the change information such as the focal extension amount α and/or the size change rate and corrects the data relating to the position and/or the size of the imaging subject when an imaging subject such as a cell C is imaged via the light transmitting member. Thus, even when the optical path refracts due to the interposition of the light transmitting member and the focal extension (condition change in the imaging) and/or the change in the imaging subject (size change) on the image occurs, such change is eliminated by the correction, whereby it becomes possible to determine the position and/or the size accurately.

Note that the first to third exemplified applications demonstrate examples to determine the focal extension amount α as the change information while the fourth exemplified application demonstrates an example to determine the size change rate. These may be determined in a combined manner. For example, in the first to third exemplified applications, the size change rate demonstrated in the fourth exemplified application may additionally be determined.

The embodiment specifically described above mainly includes the disclosure having the following configurations/features.

One aspect of the present disclosure provides an imaging system including: an imaging device configured to image an imaging subject on an imaging optical axis; and a calculation unit configured to acquire data relating to a position and/or a size of the imaging subject based on image information acquired by the imaging device through the imaging, in which the calculation unit acquires change information relating to condition change in the imaging and/or change in the imaging subject on the image, the change being caused by interposition of a light transmitting member when the light transmitting member is interposed on the imaging optical axis during the imaging, and the calculation unit corrects the data based on the change information.

According to this imaging system, the calculation unit acquires the change information and corrects the data relating to the position and/or the size of the imaging subject when the light transmitting member is interposed in the imaging. Thus, even when the optical path refracts due to the interposition of the light transmitting member and the condition change in the imaging and change in the imaging subject on the image occur, such change is eliminated, whereby it becomes possible to acquire the data with accuracy.

In the imaging system introduced above, desirably, the change information is a focal extension amount determined by a focal position of the imaging device with respect to the imaging subject when the light transmitting member is not interposed and a focal position of the imaging device with respect to the imaging subject when the light transmitting member is interposed.

When the light transmitting member is interposed on the imaging optical axis, the focal distance extends by the refraction of light passing through the light transmitting member. The imaging system can correct the data accurately as it handles the focal extension amount as the change information. The focal extension amount may be actually measured using the imaging system or other imaging devices or it may be calculated based on the physical property such as the refractive index of the light transmitting member.

In the imaging system, desirably, the change information is a change rate between an actual size of the imaging subject and a size of the imaging subject on an image acquired by the imaging device when the light transmitting member is interposed.

When the light transmitting member has a curved surface, for example, a light image of the imaging subject passed through the light transmitting member is observed in a deformed shape with respect to the actual shape thereof. The imaging system can correct the data accurately as the change rate of size is handled as the change information. Note that the change rate may be actually measured using the imaging system or other imaging devices or it may be calculated based on the curved surface and the like of the light transmitting member.

Desirably, the imaging system further includes an imaging control part configured to control operation of the imaging device. In the imaging system, the imaging control part causes the imaging device to image the imaging subject for a plurality of times while a relative distance with respect to the imaging subject is changed in a condition that the light transmitting member is interposed on the imaging optical axis, and the calculation unit determines the focal extension amount for the imaging subject based on image information acquired by the imaging of a plurality of times.

With this imaging system, it becomes possible to determine the focal extension amount by the actual measurement using the imaging device included in the imaging system. Thus, the focal extension amount can be determined with swiftness and accuracy, and additionally an extra cost for determining the focal extension amount can be avoided.

Desirably, the imaging system further includes an imaging control part configured to control operation of the imaging device. In the imaging system, the imaging subject is a tip end opening of a tip that suctions and discharges an object, and the imaging device is configured to image the tip end opening via the light transmitting member, the imaging control part causes the imaging device to image a zone including at least the tip end opening of the tip for a plurality of times while a relative distance with respect to the tip is changed in a condition that the light transmitting member is interposed on the imaging optical axis, and the calculation unit determines the focal extension amount for the tip end opening based on image information acquired by the imaging of a plurality of times.

According to the imaging system, the focal extension amount can be easily determined with the in-focus image of the tip end opening of the tip identified from the image information acquired by the imaging of a plurality of times with the light transmitting member being interposed and with the comparison between the focal distance when the in-focus image is acquired and the focal distance when the light transmitting member is not interposed.

It is desirable that the imaging system further includes an imaging control part configured to control operation of the imaging device. In the imaging system, the light transmitting member has a first surface and a second surface opposite the first surface and is a light transmitting container including in the first surface side a retaining part for retaining the imaging subject, and the imaging device is configured to image the imaging subject from the second surface side of the container, the imaging control part causes the imaging device to image a zone including at least the retaining part of the container for a plurality of times while a relative distance with respect to the container is changed on the imaging optical axis, and the calculation unit determines the focal extension amount for the retaining part based on image information acquired by the imaging of a plurality of times.

With this imaging system, the focal extension amount can be easily determined from the image information acquired by the imaging of a plurality of times, in which the in-focus image of the retaining part passed through the container identified as the light transmitting member is acquired and the focal distance of the acquired in-focus image is compared with a focal distance in a state that the container is not interposed.

In the imaging system, it is desirable that the light transmitting member includes, in addition to the container, a light transmitting base on which the container is mounted, and the imaging device is configured to image the container through the base.

With this imaging system, the focal extension amount of complexity caused by the container and the base interposed on the imaging optical axis can be easily determined by the actual measurement using the imaging device.

In the imaging system, the retaining part may be supported apart from a bottom wall of the container, and the light transmitting member further includes light transmitting fluid injected into the container so that the retaining part is immersed.

With this imaging system, the focal extension amount can be easily determined by the actual measurement using the imaging device, in which the focal extension amount has complexity caused by, on the imaging optical axis, the interposition of two objects, which are the container and the light transmitting fluid, or the interposition of three objects, which are the container, base and the light transmitting fluid.

It is desirable that the imaging system further includes an imaging control part configured to control operation of the imaging device. In the imaging system, the light transmitting member has a first surface and a second surface opposite the first surface and is a light transmitting container including in the first surface side a retaining part for retaining the imaging subject, the retaining part having an optical effect to deform a light image, and the imaging device is configured to image the imaging subject from the second surface side of the container, and the imaging control part causes the imaging device to image a zone including at least the retaining part of the container with a predetermined distance on the imaging optical axis with respect to the container that includes the retaining part in which a test subject of known size is retained, and the calculation unit determines the change rate by a comparison between a size of the test subject determined from an image acquired by the imaging and the known size.

With this imaging system, it becomes possible to determine how the size has changed due to the optical path actually passed through the container having the optical effect by the comparison between the size of the test subject determined by the captured image and the known size thereof. Thus, the change rate can be determined with swiftness and accuracy and in addition, an extra cost for determining the change rate can be excluded.

Desirably, in this case, the imaging control part causes the imaging device to carry out the imaging in which the test subject in the retaining part is arranged to have different retaining positions, and the calculation unit determines the change rate for each of the retaining positions.

The container and the retaining part may have various change rates depending on the retaining positions and their shapes. The imaging system determines the change rate for each of the retaining positions, which allows the correction corresponding to each of the retaining positions.

It is a desirable application and usage of the imaging system of the present disclosure in which the imaging subject or the object is a cell or a cell aggregate.

The present disclosure described above can provide an imaging system that can determine the position and/or the size of the imaging subject with accuracy even when the imaging subject is imaged through the light transmitting member interposed on the imaging optical axis.

What is claimed is:

1. An imaging system comprising:
an imager configured to image an imaging subject on an imaging optical axis; and
a calculator configured to acquire data relating to a position and/or a size of the imaging subject based on image information acquired by the imager through the imaging, such that the calculator acquires change information relating to condition change in the imaging and/or change in the imaging subject on the image, the change being caused by interposition of a light transmitting member when the light transmitting member is interposed on the imaging optical axis during the imaging, and the calculator corrects the data based on the change information,
wherein the change information is a focal extension amount determined by a focal position of the imager with respect to the imaging subject when the light transmitting member is not interposed and a focal position of the imager with respect to the imaging subject when the light transmitting member is interposed, and
the imaging system further comprising an imaging controller configured to control operation of the imager, wherein
the imaging subject is a tip end opening of a tip that suctions and discharges an object, and the imager is configured to image the tip end opening via the light transmitting member,
the imaging controller causes the imager to image a zone including at least the tip end opening of the tip for a plurality of times while a relative distance with respect to the tip is changed in a condition that the light transmitting member is interposed on the imaging optical axis, and
the calculator determines the focal extension amount for the tip end opening based on image information acquired by the imaging of a plurality of times.

2. An imaging system comprising:
an imager configured to image an imaging subject on an imaging optical axis; and
a calculator configured to acquire data relating to a position and/or a size of the imaging subject based on image information acquired by the imager through the imaging, such that the calculator acquires change information relating to condition change in the imaging and/or change in the imaging subject on the image, the change being caused by interposition of a light transmitting member when the light transmitting member is interposed on the imaging optical axis during the imaging, and the calculator corrects the data based on the change information,
wherein the change information is a focal extension amount determined by a focal position of the imager with respect to the imaging subject when the light transmitting member is not interposed and a focal position of the imager with respect to the imaging subject when the light transmitting member is interposed, and
the imaging system further comprising an imaging controller configured to control operation of the imager, wherein
the light transmitting member has a first surface and a second surface opposite the first surface and is a light transmitting container including in the first surface side a retainer configured to retain the imaging subject, and the imager is configured to image the imaging subject from the second surface side of the container,
the imaging controller causes the imager to image a zone including at least the retainer of the container for a plurality of times while a relative distance with respect to the container is changed on the imaging optical axis, and
the calculator determines the focal extension amount for the retainer based on image information acquired by the imaging of a plurality of times.

3. The imaging system according to claim 2, wherein the light transmitting member includes, in addition to the container, a light transmitting base on which the container is mounted, and
the imager is configured to image the container through the base.

4. The imaging system according to claim 2, wherein
the retainer is supported apart from a bottom wall of the container, and
the light transmitting member further includes light transmitting fluid injected into the container so that the retainer is immersed.

5. An imaging system comprising:
an imager configured to image an imaging subject on an imaging optical axis; and
a calculator configured to acquire data relating to a position and/or a size of the imaging subject based on image information acquired by the imager through the imaging, such that the calculator acquires change information relating to condition change in the imaging and/or change in the imaging subject on the image, the change being caused by interposition of a light transmitting member when the light transmitting member is interposed on the imaging optical axis during the imaging, and the calculator corrects the data based on the change information, wherein
the change information is a change rate between an actual size of the imaging subject and a size of the imaging subject on an image acquired by the imager when the light transmitting member is interposed, and
the imaging system further comprising an imaging controller configured to control operation of the imager, wherein
the light transmitting member has a first surface and a second surface opposite the first surface and is a light transmitting container including in the first surface side a retainer configured to retain the imaging subject, the retainer having an optical effect to deform a light image, and the imager is configured to image the imaging subject from the second surface side of the container, and
the imaging controller causes the imager to image a zone including at least the retainer of the container with a predetermined distance on the imaging optical axis with respect to the container that includes the retainer in which a test subject of known size is retained, and
the calculator determines the change rate by a comparison between a size of the test subject determined from an image acquired by the imaging and the known size.

6. The imaging system according to claim 5, wherein
the imaging controller causes the imager to carry out the imaging in which the test subject in the retainer is arranged to have different retaining positions, and
the calculator determines the change rate for each of the retaining positions.

7. The imaging system according to claim 2, wherein the imaging subject is a cell or a cell aggregate.

8. The imaging system according to claim 1, wherein the object is a cell or a cell aggregate.

* * * * *